United States Patent
Church et al.

(10) Patent No.: US 10,517,629 B2
(45) Date of Patent: Dec. 31, 2019

(54) DISPOSABLE DEBRIDER WITH CANNULATED SOLENOID

(71) Applicant: Gyrus ACMI, Inc., Southborough, MA (US)

(72) Inventors: David Church, Millington, TN (US); Ahmad Alsaffar, Bartlett, TN (US); Daniel Goldberg, Memphis, TN (US); Joel Willhite, Memphis, TN (US); Kevin Edwards, Olive Branch, MS (US)

(73) Assignee: Gyrus ACMI, Inc., Southborough, MA (US)

( * ) Notice: Subject to any disclaimer, the term of this patent is extended or adjusted under 35 U.S.C. 154(b) by 0 days.

(21) Appl. No.: 15/880,998

(22) Filed: Jan. 26, 2018

(65) Prior Publication Data
US 2019/0231378 A1    Aug. 1, 2019

(51) Int. Cl.
| A61B 17/3205 | (2006.01) |
| A61B 17/24 | (2006.01) |
| A61B 17/32 | (2006.01) |
| A61B 17/00 | (2006.01) |
| A61B 18/14 | (2006.01) |
| A61B 18/00 | (2006.01) |

(52) U.S. Cl.
CPC .......... *A61B 17/3205* (2013.01); *A61B 17/24* (2013.01); *A61B 17/32002* (2013.01); *A61B 18/14* (2013.01); *A61B 2017/0023* (2013.01); *A61B 2017/00398* (2013.01); *A61B 2017/00862* (2013.01); *A61B 2017/246* (2013.01); *A61B 2017/320028* (2013.01); *A61B 2018/00601* (2013.01)

(58) Field of Classification Search
CPC ............... A61B 17/24; A61B 17/3205; A61B 2017/0023; A61B 2017/00398; A61B 2017/00862; A61B 2017/246; A61B 2018/00601; A61B 18/14; A61B 17/32037; A61B 17/320016; A61B 17/320758; A61B 17/320725; A61B 17/32075; A61B 17/320783; A61B 17/32002; A61B 2017/320775
See application file for complete search history.

(56) References Cited

U.S. PATENT DOCUMENTS 3,054,464 A * 9/1962 Ondeck ................ B25D 11/064
                                                                173/104
3,201,670 A * 8/1965 Myers .................... H02K 33/12
                                                                310/30

(Continued)

FOREIGN PATENT DOCUMENTS

WO    2015061643 A2    4/2015

OTHER PUBLICATIONS

"Thunderbeat Generators". Retrieved Jan. 25, 2018, from http://medical.olympusamerica.com/products/thunderbeat-generators-esg-400-usg-400, 2 pages.

(Continued)

*Primary Examiner* — Tuan V Nguyen
(74) *Attorney, Agent, or Firm* — Harrington & Smith

(57) ABSTRACT

Disclosed herein is a medical device. The medical device includes two coaxially aligned solenoids and a cannulated armature configured to be received within the two coaxially aligned solenoids.

19 Claims, 7 Drawing Sheets

(56) References Cited

U.S. PATENT DOCUMENTS

| | | | |
|---|---|---|---|
| 6,258,111 B1* | 7/2001 | Ross | A61B 17/32002 606/171 |
| 6,293,957 B1 | 9/2001 | Peters et al. | |
| 7,226,459 B2 | 6/2007 | Cesarini et al. | |
| 7,510,563 B2 | 3/2009 | Cesarini et al. | |
| 7,666,200 B2 | 2/2010 | Heisler | |
| 8,286,899 B2 | 10/2012 | Schowalter et al. | |
| 2008/0208233 A1* | 8/2008 | Barnes | A61F 9/00763 606/171 |

OTHER PUBLICATIONS

"Disposable Tonsil Adenoid Debrider". Retrieved Jan. 25, 2018, from http://medical.olympusamerica.com/products/debrider/dtad-70138400, 1 page.

"PolypVac". Retrieved Jul. 20, 2017, from https://zc1.campaign-view.com/ua/viewinbrowser?od=11287eca5dbc3b&rd=119f933bb603779b&sd=119f933bb6033495&n=11699e4beebbffe&mrd=119f933bb6033487&m=1, 2015, 2 pages.

"Straightshot M5 Microdebrider". Retrieved Jan. 25, 2018, from http://www.medtronic.com/for-healthcare-professionals/business-unit-landing-Page/straightshot-m5-30k-burs/index.htm, 1 page.

"Straightshot M4 Microdebrider". Retrieved Jan. 25, 2018, from http://www.medtronic.com/us-en/healthcare-professionals/products/ear-nose-throat/powered-ent-instruments/powered-ent-instruments/handpieces-accessories.html, 1 page.

"Multidebrider Diego Elite". Retrieved Jan. 25, 2018, from http://medical.olympusamerica.com/products/debrider/diego%C2%AE-elite, 2 pages.

"Hightlights 2017 Otorhinolaryngology". Edition Jan. 2017. Retrieved Jan. 25, 2018, from https://www.karlstorz.com/cps/rde/xbcr/karistorz_assets/ASSETS/3482434.pdf, 20 pages.

"ConMed". Retrieved Jan. 25, 2018, from http://www.conmed.com/en/products/orthopedics/ablation/bipolar-ablation/edge-bipolar-arthroscopic-rf-system, 2 pages.

"Smith & Nephew". Retrieved Jan. 25, 2018, from http://www.smith-nephew.com/professional/products/all-products/dyonics-power-ii-control-system/, 2 pages.

"ESSx Microdebrider". 2007. Retrieved Jan. 25, 2018, from https://nse.stryker.com/wp-content/uploads/2016/09/ESSx-Microdebrider-brochure.pdf, 2 pages.

* cited by examiner

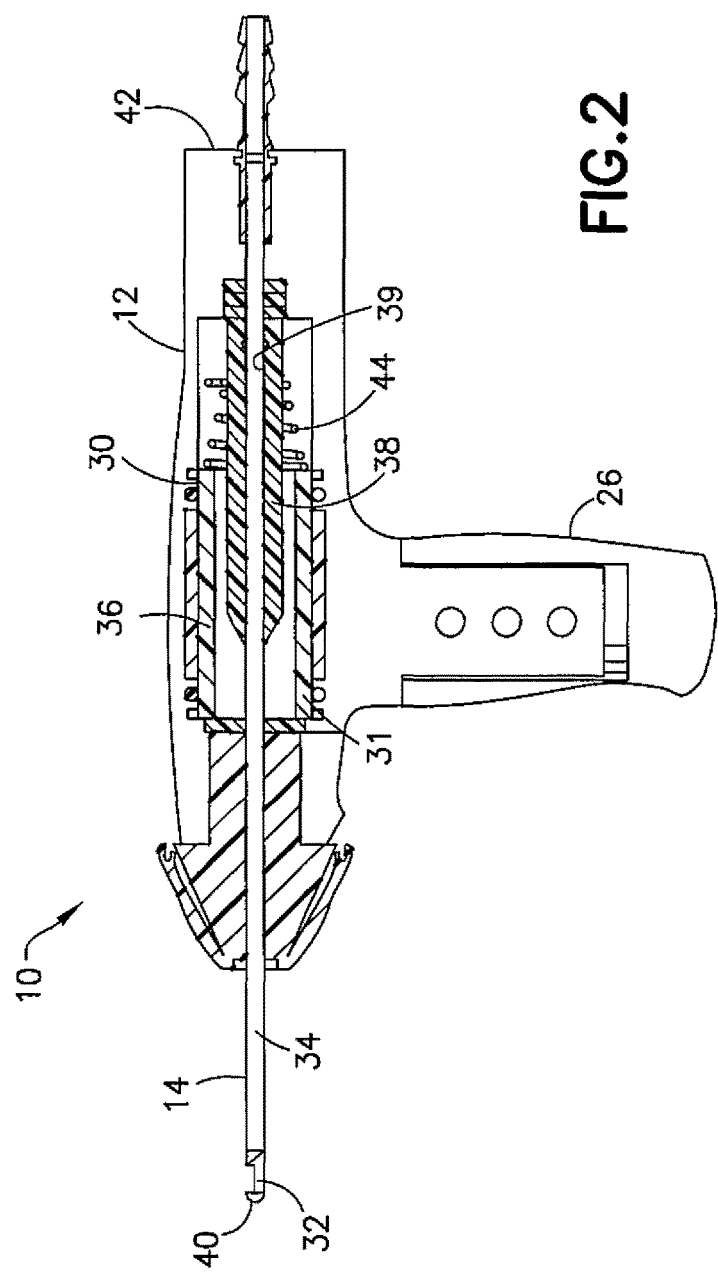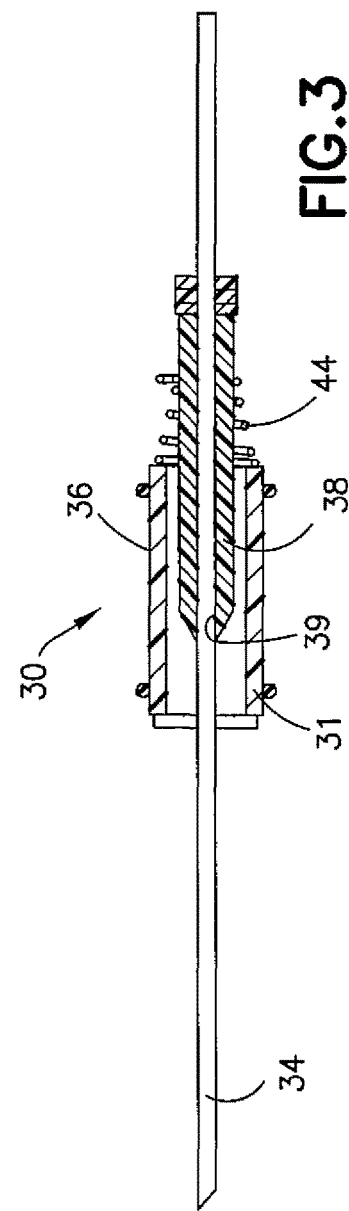

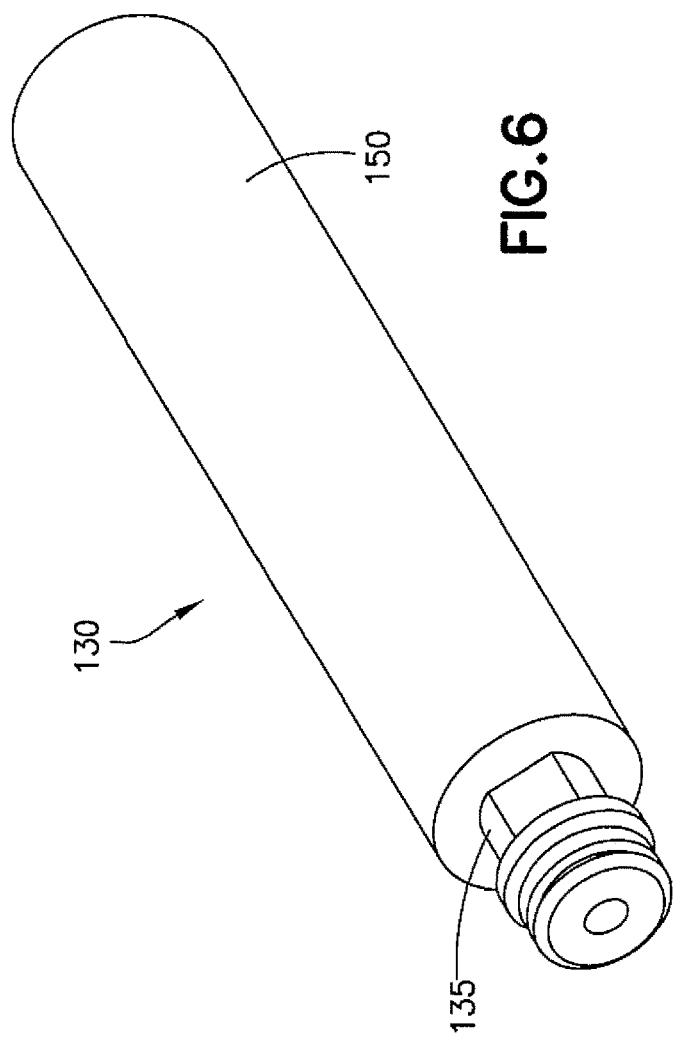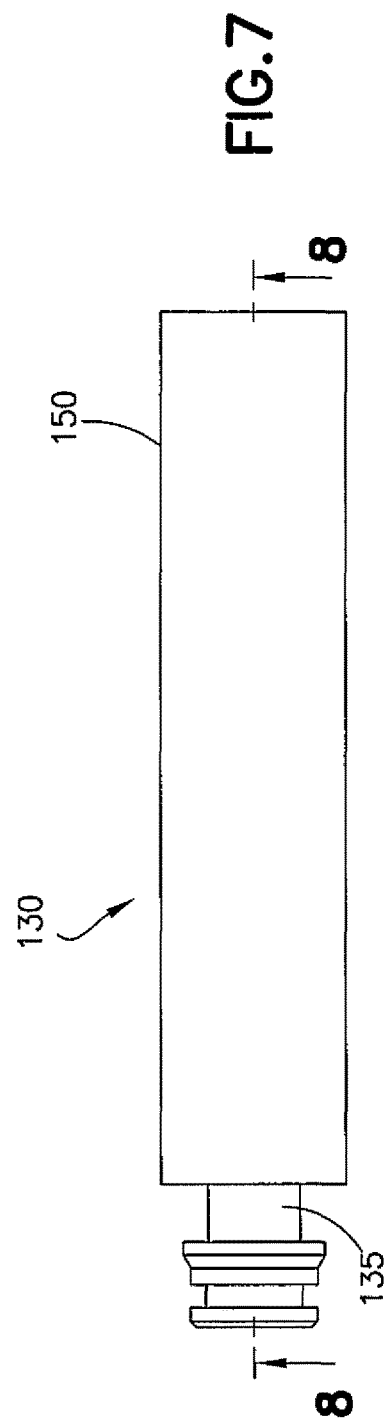

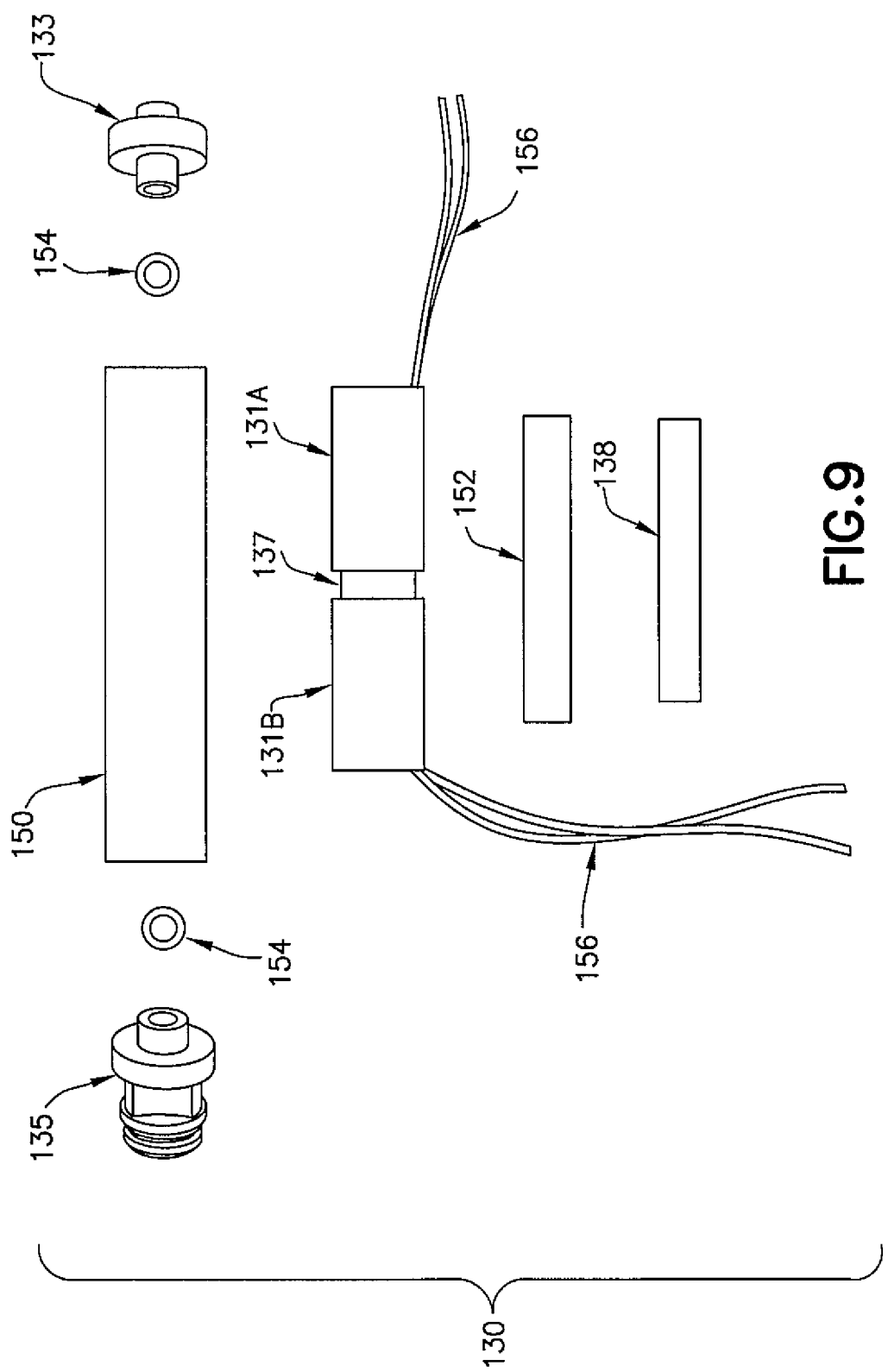

DISPOSABLE DEBRIDER WITH CANNULATED SOLENOID

BACKGROUND

Field of the Invention

The invention relates to a medical device and more specifically relates to a disposable debrider with a cannulated solenoid.

Brief Description of Prior Developments

Conventional shavers generally use a rotational motor coupled with a parallel gear train to impart oscillatory motion. For example, PolypVac (manufactured by Laurimed) uses reciprocating cutting motion, presumably powered by Suction (mechanism unknown). Other known ideas are worm gears and 'levelwind gears' or 'diamond screws'. All of these known technologies involve multiple moving components in which a power source, often rotational, translates the input motion to a linear repeating cutting motion. This reciprocating motion has limitations in that it is often complex relative to oscillatory or rotational cutting, and it doesn't lend well to curved devices. This complexity is often quite expensive and may be tedious to manufacture, particularly in disposable devices. Additionally, since most shaver systems encompasses both blades and burrs, reciprocation is not a good choice for durable equipment because its limitation is supporting drilling and curved devices.

The PolypVac mechanism uses operating room or office-equipped vacuum suction to create and power the cutting motion. Because medical suction devices are of varying quality, strengths and reliabilities, cutting performance and efficiency is often lacking in both power of cutting motion and repeatability of the performance, particularly in the cost-sensitive package of a disposable device. Ostensibly, the mechanical complexity of such a mechanism packaged for one-time use is also subject to quality and reliability problems in the field. Additionally, it's believed that the vacuum pressure used to power the device subtracts from the critical aspiration power needed to engage and pull tissue in to the cutting window. Aspiration can be a critical input feature of a Microdebrider with respect to cutting performance.

Accordingly, there is a need to provide improved and reliable medical device configurations.

SUMMARY

In accordance with one aspect of the invention, a medical device is disclosed. The medical device includes two coaxially aligned solenoids and a cannulated armature configured to be received within the two coaxially aligned solenoids.

In accordance with another aspect of the invention, a medical device is disclosed. The medical device includes two solenoids, a cannulated armature, an inner tubular member, and an outer tubular member. The two solenoids are configured to be linearly spaced apart by a spacer. The cannulated armature is configured to be received within the two solenoids. The inner tubular member has a distal end and an open window disposed at the distal end. The inner tubular member is configured to be received within the cannulated armature. The outer tubular member having a distal end and an open window disposed at the distal end. The open window of the inner tubular member and the open window of the outer tubular member form a cutting tool.

In accordance with another aspect of the invention, a medical device is disclosed. The medical device includes a handle, two separate solenoids, a cannulated armature, an inner tubular member, and an outer tubular member. The two separate solenoids are configured to be stationary inside the handle. The cannulated armature is configured to be received within the two solenoids. The inner tubular member has a distal end and an open window disposed at the distal end. The inner tubular member is configured to be received within the cannulated armature. The outer tubular member has a distal end and an open window disposed at the distal end. The open window of the inner tubular member and the open window of the outer tubular member form a cutting tool.

BRIEF DESCRIPTION OF THE DRAWINGS

The foregoing aspects and other features of the invention are explained in the following description, taken in connection with the accompanying drawings, wherein:

FIG. 2 is a section view medical device shown in FIG. 1;

FIG. 3 is section view of a portion of the device shown in FIG. 2;

FIG. 6 is a perspective view of a solenoid assembly of the medical device shown in FIGS. 4 and 5;

FIG. 7 is a side view of the solenoid assembly shown in FIG. 6;

FIG. 9 is an exploded perspective view of the solenoid assembly shown in FIG. 6.

DETAILED DESCRIPTION

Figure 1:
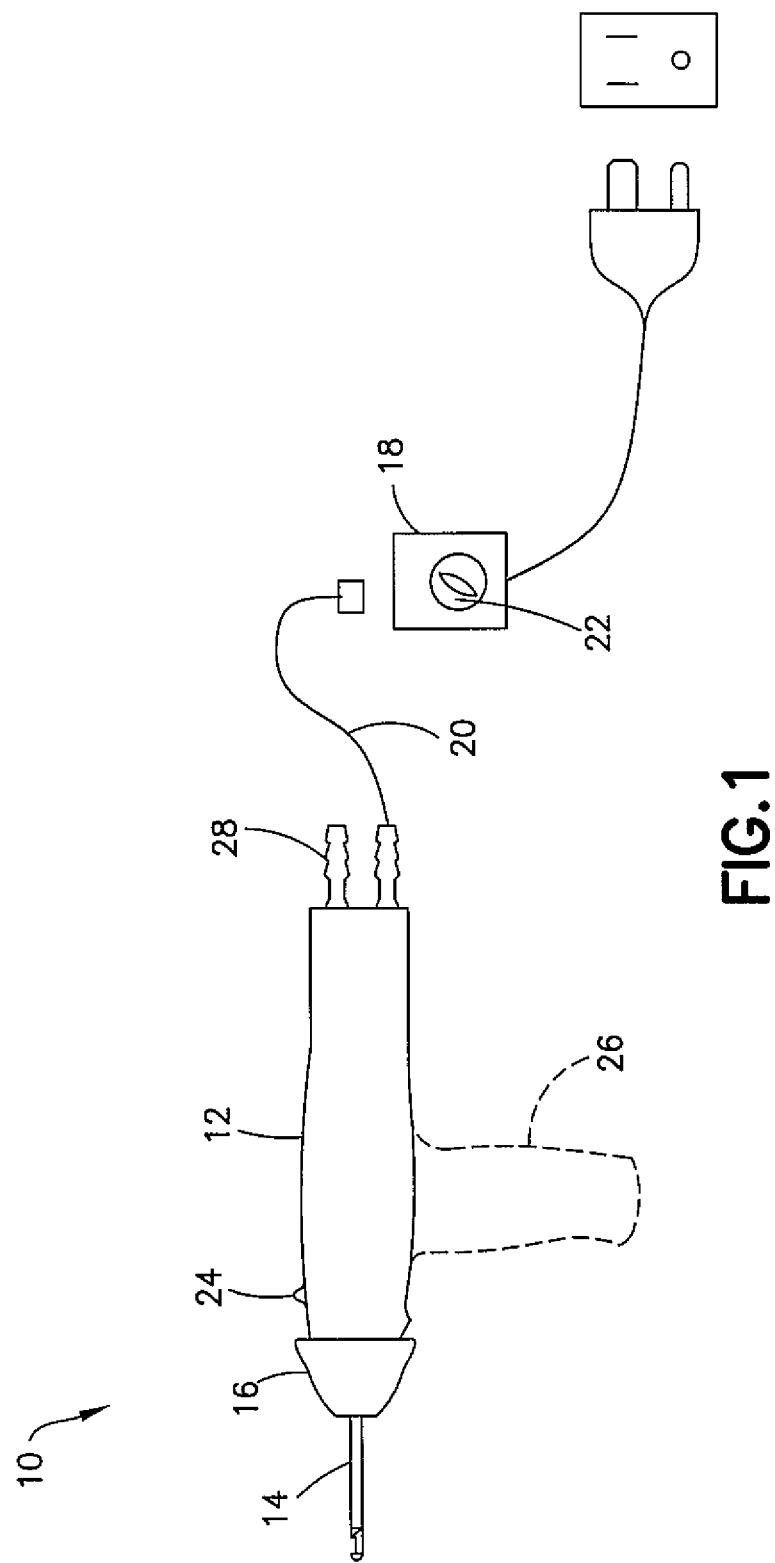
FIG. 1 is a perspective view of a medical device incorporating features of the invention.

Referring to FIG. 1, there is shown a perspective view of a medical device 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

According to various exemplary embodiments, the medical device 10 is configured for use in the removal of nasal polyps, sub-mucosal debulk of turbinates, and functional endoscopic sinus surgery (FESS), primarily in the office environment and/or cost-sensitive regions.

The medical device 10, which may be a disposable debrider for example, comprises a housing (which may form a handpiece portion) 12, a blade tube section 14, and a nosecone 16. The nosecone 16 may be a rotatable nosecone and is between the housing 12 and the blade tube section 14. However it should be noted that exemplary embodiments of the medical device may comprise any suitable configuration such as configurations having a nosecone coupled to an outer member (of the housing), or any other suitable curved or straight debrider configuration which may comprise an irrigation feature, for example. The medical device 10 is configured to be connected to a reusable power supply 18 (which may have a similar physical size to that of a laptop computer power supply, for example) which is used to power the device 10 and may be universally compatible with all worldwide wall power supplies and plug styles. A length of disposable power cord 20 may be attachable to the handpiece portion 12 and plugs in to the power supply 18. A user-selectable speed dial 22 may also be provided on the power supply 18. The blade tube section 14 of the device 10 can be configured with large and small shaver tubes, depending on anatomy and surgeon preference, and can also be adapted for bipolar (preferred) or monopolar radio-frequency (RF) power. An external ESG (electrosurgical generator) may supply the RF power, for example. A shaver activation button 24 is located on the housing 12 in an ergonomic location to power and control the shaver blade. However, in alternate embodiments the shaver activation button may be provided on a handle portion 26 attached to the housing 12, or activated by a separate footswitch (instead of a button on the housing). Additionally, a suction connection 28 for a tube may be provided adjacent the power cord.

Referring now also to FIGS. 2 and 3, the medical device 10 further comprises a solenoid 30 mounted in the housing 12 on the main blade and aspiration pathway axis, and the blade tube section 14 comprises an outer blade tube 32 and an inner blade tube 34.

The solenoid 30 comprises a static hollow cylindrical section 36 with an energizing coil 31, and a dynamic "plunger" piece 38 in the center of the hollow static section that is inducted to move axially with a known force when the coil 31 is electrically energized. This provides for the medical device 10 to generally include only one moving part. The plunger 38 comprises a hole (or opening) 39 extending along a central axis of the plunger 38. The opening 39 is configured to receive the inner blade tube 34 such that the inner blade tube 34 is fixed to the plunger 38.

The outer blade tube 32 is (rotatably or fixedly) mounted to the housing 12 and acts as a static member, wherein the inner blade tube 34 is slidably mounted inside the outer blade tube 32. When the coil 31 is energized, the inner blade tube 34 is then forced distally [i.e. towards the distal end 40] (or proximally [i.e. towards the proximal end 42] depending on the construction, choice of solenoid type, and desired cutting motion) to cut tissue. One or more springs 44 are provided to return the plunger 38 to its 'home' position with a biasing force of the spring(s) 44. The center aspiration pathway is then created by the inner blade/tube lumen and the inner lumen of the plunger piece. Additionally, in some embodiments of the shaver tip window geometry, the inner blade is rotatably coupled to the outer blade tube.

Figure 4:
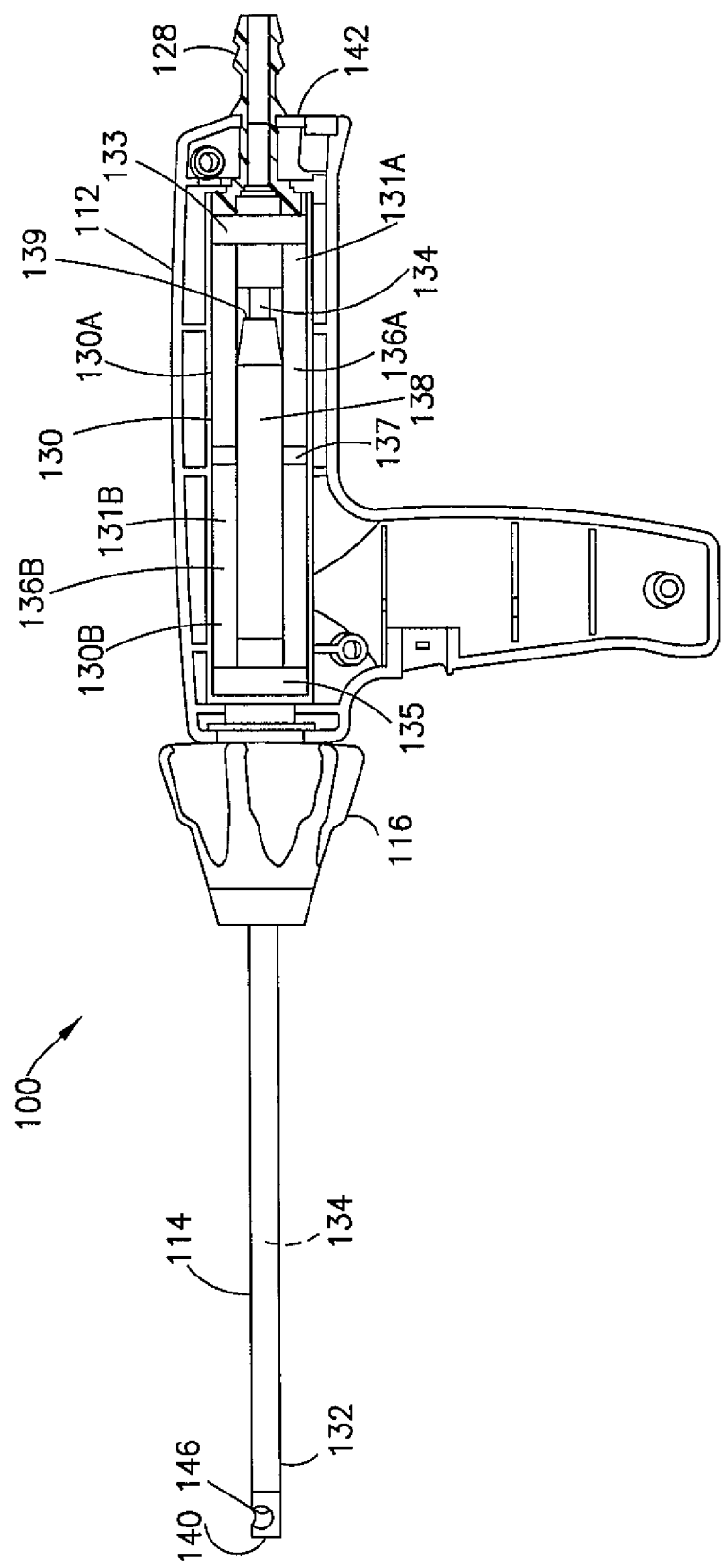
FIGS. 4 and 5 are section views of another example medical device incorporating features of the invention.
Figure 5:
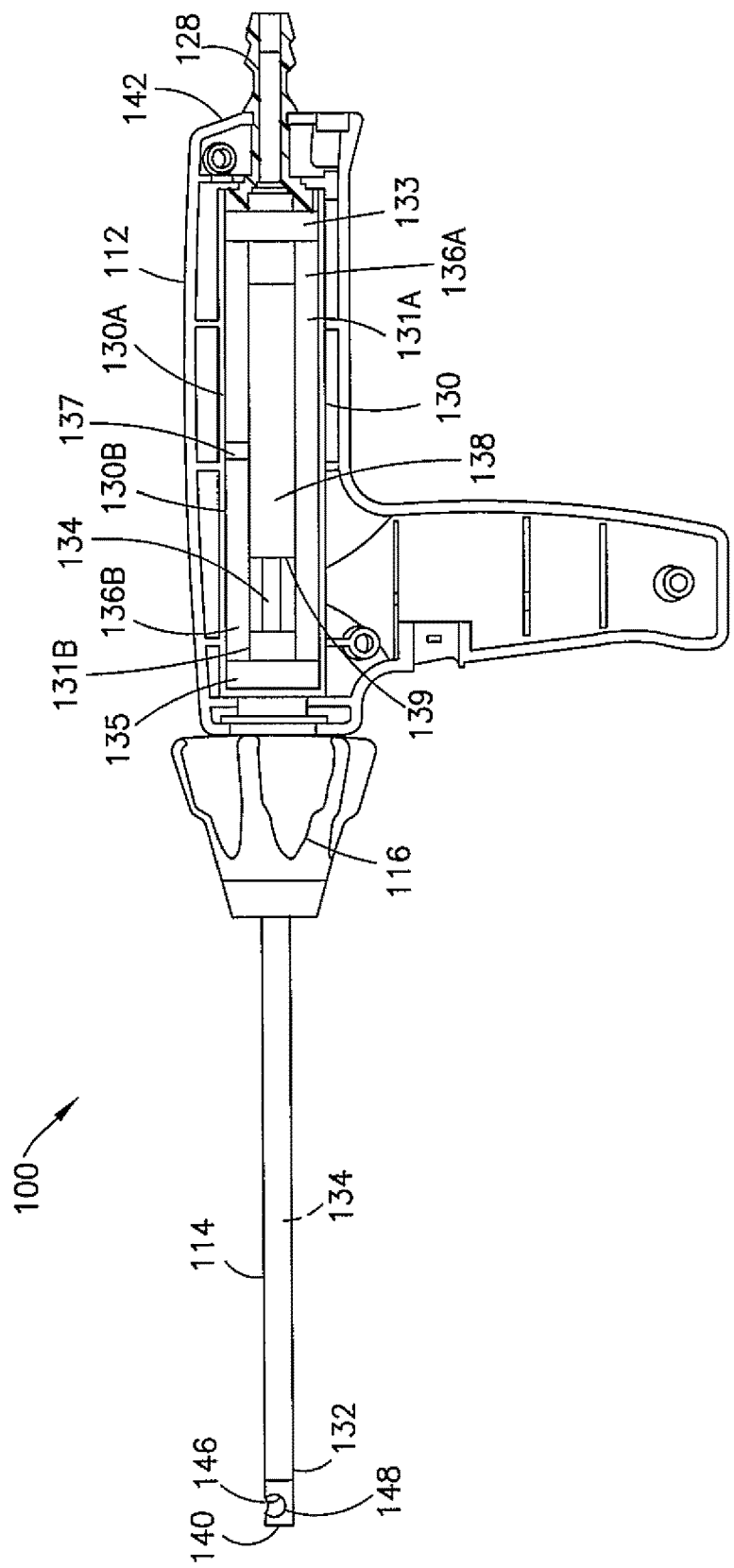
Figure 8:
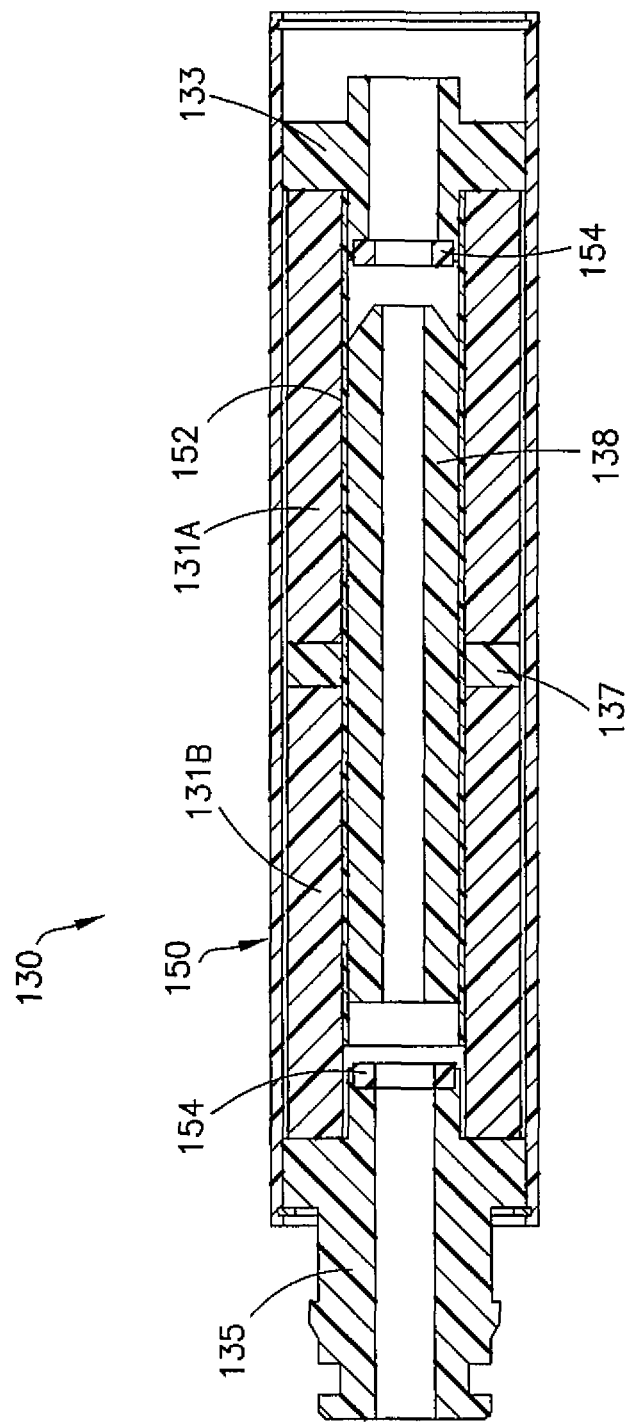
FIG. 8 is a section view of the solenoid assembly shown in FIGS. 6 and 7.

Referring now also to FIGS. 4 and 5, another embodiment of a medical device is shown. The medical device 100 shown in FIGS. 4 and 5 is similar to the medical device 10 (shown in FIGS. 1-3) and similar features are similarly numbered. However, instead of using one solenoid that is energized for the "power" stroke with a spring to achieve the return stroke (as in FIGS. 1-3), the medical device 100 uses two opposing solenoids.

Similar to the medical device 10, the medical device 100 comprises a housing 112, a blade tube section 114, a nosecone 116, and a handle 126. The nosecone 116 may be a rotatable nosecone and is between the housing 112 and the blade tube section 114. Additionally, the medical device 100 comprises a suction connection 128 (which may be coaxial or off-axis with the solenoid axis) and a power cord connection [not shown].

The medical device 100 further comprises a dual solenoid assembly 130 mounted in the housing 112 on the main blade and aspiration pathway axis, and the blade tube section 114 comprises an outer blade tube 132 and an inner blade tube 134.

The dual solenoid assembly 130 comprises opposing solenoids 130A, 130B, linearly spaced between a proximal endcap 133 and a distal endcap 135, and separated by a coil spacer 137. The solenoid 130A is between the coil spacer 137 and the proximal endcap 133. The solenoid 130B is between the coil spacer 137 and the distal endcap 135. The solenoid 130A comprises a static hollow cylindrical section 136A and an energizing coil 131A. Similarly, the solenoid 130B comprises a static hollow cylindrical section 136B and an energizing coil 131B.

A cannulated armature 138 is configured to be received within the hollow cylindrical sections of the solenoids 130A, 130B. The cannulated armature 138 comprises a cylindrical shape and is configured to be movable between the endcaps 133, 135. The cannulated armature 138 comprises a hole (or opening) 139 extending along a central axis of the armature 138. The opening 139 is configured to receive the inner blade tube 134 such that the inner blade tube 134 is fixed to the armature 138. The cannulated armature 138 is configured to be driven by the solenoids 130A, 130B to reciprocate between the endcaps 133, 135.

According to various exemplary embodiments, the outer blade tube and the inner blade tube each comprise an open window (146, 148, respectively) at a distal end 140 of the device 100. However, in some alternate embodiments only the outer blade tube comprises an open window. It should further be noted that although various exemplary embodiments of the invention have been described in connection with the inner and/or outer blade tube as having an open window, alternate embodiments may comprise inner and/or outer blade tubes having two or more windows.

The outer blade tube 132 is mounted to the housing 112 and acts as a static member, wherein the inner blade tube 134 is slidably mounted inside the outer blade tube 132. The open windows 146, 148 at the distal end provide a cutting feature for the medical device 100, as the cannulated armature 138 is configured to be driven by the solenoids 130A, 130B (when the coils 131A, 131B are electrically energized) to reciprocate the inner blade tube 134 to perform tissue cuts (by bringing the window 148 of the inner blade tube 134 into alignment and out of alignment with the window 146 of the outer blade tube 132).

For example, when the coil 131B is energized this induces the movement of the armature 138 distally [i.e. towards the distal end 140] for the power stroke (or forward stroke direction) and the attached inner blade tube 134 is also forced distally (see FIG. 4 where the device cutting window is closed [by having the inner blade tube at a position closest to the distal end] and the armature is at the end of the power stroke [and proximate the distal end cap 135]). Similarly, when the coil 131A is energized this induces the movement of the armature 138 proximally [i.e. towards the proximal end 142] for the return stroke (or reverse stroke direction) and the attached inner blade tube 134 is also forced proximally (see FIG. 5 where the device cutting window is open [by having the inner blade tube at a position closest to the proximal end] and the armature 138 is at the end of the return stroke [and proximate the proximal end cap 133]).

According to various exemplary embodiments, the solenoid assembly 130 comprises a casing 150 surrounding the solenoid coils 131A, 131B and the coil spacer 137 (best shown in FIGS. 6-9). The casing 150 comprises a general tubular shape and is configured to receive the proximal end cap 133 at one end and the distal end cap 135 at an opposite end. The solenoid assembly 130 may further comprise an armature sleeve (or brass guide tube) 152 between the solenoid coils 131A, 131B and the armature 138. Additionally, elastomer spacers 154 may be provided between the proximal end cap 133 and a proximal end of the armature 138, and between the distal end cap 135 and a distal end of the armature 138. Further, coil wire leads 156 may extend from ends of the solenoid coils 131A, 131B, however any suitable type of power connection to the solenoid coils may be provided.

Technical effects of any one or more of the exemplary embodiments provide significant advantages over conventional configurations by providing a stronger power stroke (no energy diverted to compress a spring) and a stronger return stroke. Also, both directions of the stroke can now be controlled by the timing of current supplied to each coil, unlike the passive spring return. It should further be noted that various exemplary embodiments may comprise solenoids having different sizes and/or stroke powers. Additionally, alternate control options related to forward/backward stroke speeds, dwells, etc., may be provided.

A further technical effect of any one or more of the exemplary embodiments provides configurations which can perform each stroke (power and return) independently. This allows for a functionality which the doctor can choose "window closed" or "window open" configurations when the device is idle. This is a desirable function because many doctors want a closed window while the approach the treatment area, and then an open widow once they are near the target tissue.

Additional technical effects of any one or more of the exemplary embodiments provides an inner blade tube that is flexible (such as one fabricated from either plain or reinforced nylon tubing, or possibly PEEK tubing, for example). This feature can reduce the resistive losses between the inner and outer blade tubes when the outer blade tube is subjected to side loading, thus keeping the cutting stroke powerful and allows for curved or malleable embodiments.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical device comprising two coaxially aligned solenoids and a cannulated armature configured to be received within the two coaxially aligned solenoids.

A medical device as above, wherein the two coaxially aligned solenoids are linearly spaced.

A medical device as above, further comprising an inner tubular member having a distal end and an open window disposed at the distal end, the inner tubular member configured to be received within the cannulated armature.

A medical device as above, further comprising an outer tubular member having a distal end and an open window disposed at the distal end, wherein the open window of the inner tubular member and the open window of the outer tubular member form a cutting tool.

A medical device as above, further comprising a metal spacer between the two coaxially aligned solenoids.

A medical device as above, wherein further comprising a casing, wherein the two coaxially aligned solenoids are between the cannulated armature and the casing.

A medical device as above, further comprising a proximal endcap and a distal endcap, wherein the proximal endcap is received by one end of the casing, and wherein the distal endcap is received by an opposite end of the casing.

A medical device as above, wherein the medical device comprises only two coaxially aligned solenoids.

In another exemplary embodiment, a medical device, comprising: two solenoids configured to be linearly spaced apart by a spacer; a cannulated armature configured to be received within the two solenoids; an inner tubular member having a distal end and an open window disposed at the distal end, the inner tubular member configured to be received within the cannulated armature; and an outer tubular member having a distal end and an open window disposed at the distal end, wherein the open window of the inner tubular member and the open window of the outer tubular member form a cutting tool.

A medical device as above, further comprising a casing, wherein the two solenoids are between the cannulated armature and the casing.

A medical device as above, further comprising a proximal endcap and a distal endcap, wherein the proximal endcap is received by one end of the casing, and wherein the distal endcap is received by an opposite end of the casing.

A medical device as above, wherein the cannulated armature is configured to be movable relative to the two solenoids.

A medical device as above, further comprising an armature sleeve between the cannulated armature and the two solenoids.

A medical device as above, further comprising a first elastomer spacer and a second elastomer spacer, wherein the cannulated armature is between the first elastomer spacer and the second elastomer spacer.

In another exemplary embodiment, a medical device, comprising: a handle; two separate solenoids configured to be stationary inside the handle; a cannulated armature configured to be received within the two solenoids; an inner tubular member having a distal end and an open window disposed at the distal end, the inner tubular member configured to be received within the cannulated armature; and an outer tubular member having a distal end and an open window disposed at the distal end, wherein the open window of the inner tubular member and the open window of the outer tubular member form a cutting tool.

A medical device as above, further comprising a spacer between the two separate solenoids.

A medical device as above, wherein the two separate solenoids are linearly spaced.

A medical device as above, wherein the inner tubular member is configured to be movable relative to the outer tubular member.

A medical device as above, further comprising a casing, wherein the two separate solenoids are between the cannulated armature and the casing.

A medical device as above, further comprising an armature sleeve, wherein the armature sleeve is between the cannulated armature and the solenoids.

It is noted that the term "cannulated" used throughout the specification refers to a general 'tube' or 'tubular', or 'hollowed out cylindrical' shape, or any general cylinder shape having an outside diameter and an inside diameter, for example.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical device comprising:
   two coaxially aligned solenoids;
   a cannulated armature configured to be received within the two coaxially aligned solenoids, wherein the two coaxially aligned solenoids are between a proximal end cap of the medical device and a distal end cap of the medical device, wherein the cannulated armature comprises a proximal end and a distal end, wherein a portion of the proximal end cap is received within a first one of the two coaxially aligned solenoids, wherein a portion of the distal end cap is received within a second one of the two coaxially aligned solenoids; and
   a first elastomer spacer and a second elastomer spacer, wherein the first elastomer spacer is between the proximal end cap and the proximal end of the armature, and wherein the second elastomer spacer is between the distal end cap and the distal end of the armature.

2. The medical device of claim 1 wherein the two coaxially aligned solenoids are linearly spaced.

3. The medical device of claim 1 further comprising an inner tubular member having a distal end and an open window disposed at the distal end, the inner tubular member configured to be received within the cannulated armature.

4. The medical device of claim 3 further comprising an outer tubular member having a distal end and an open window disposed at the distal end, wherein the open window of the inner tubular member and the open window of the outer tubular member form a cutting tool.

5. The medical device of claim 1 further comprising a metal spacer between the two coaxially aligned solenoids.

6. The medical device of claim 1 further comprising a casing, wherein the two coaxially aligned solenoids are between the cannulated armature and the casing.

7. The medical device of claim 6, wherein the proximal endcap is received by one end of the casing, and wherein the distal endcap is received by an opposite end of the casing.

8. The medical device of claim 1 wherein the medical device comprises only two coaxially aligned solenoids.

9. A medical device, comprising:
   two solenoids configured to be linearly spaced apart by a space, wherein the two solenoids are between a proximal end cap of the medical device and a distal end cap of the medical device, wherein a portion of the proximal end cap is received within a first one of the two solenoids, wherein a portion of the distal end cap is received within a second one of the two solenoids;
   a cannulated armature configured to be received within the two solenoids, wherein the cannulated armature comprises a proximal end and a distal end;
   a first elastomer spacer and a second elastomer spacer, wherein the first elastomer spacer is between the proximal end cap and the proximal end of the armature, and wherein the second elastomer spacer is between the distal end cap and the distal end of the armature;
   an inner tubular member having a distal end and an open window disposed at the distal end, the inner tubular member configured to be received within the cannulated armature; and
   an outer tubular member having a distal end and an open window disposed at the distal end,
   wherein the open window of the inner tubular member and the open window of the outer tubular member form a cutting tool.

10. The medical device of claim 9 further comprising a casing, wherein the two solenoids are between the cannulated armature and the casing.

11. The medical device of claim 10, wherein the proximal endcap is received by one end of the casing, and wherein the distal endcap is received by an opposite end of the casing.

12. The medical device of claim 9 wherein the cannulated armature is configured to be movable relative to the two solenoids.

13. The medical device of claim 9 further comprising an armature sleeve between the cannulated armature and the two solenoids.

14. A medical device, comprising:
   a handle;
   two separate solenoids configured to be stationary inside the handle, wherein the two separate solenoids are between a proximal end cap of the medical device and a distal end cap of the medical device, wherein a portion of the proximal end cap is received within a first one of the two separate solenoids, wherein a portion of the distal end cap is received within a second one of the two separate solenoids;
   a cannulated armature configured to be received within the two solenoids, wherein the cannulated armature comprises a proximal end and a distal end;
   a first elastomer spacer and a second elastomer spacer, wherein the first elastomer spacer is between the proximal end cap and the proximal end of the armature, and wherein the second elastomer spacer is between the distal end cap and the distal end of the armature;
   an inner tubular member having a distal end and an open window disposed at the distal end, the inner tubular member configured to be received within the cannulated armature; and
   an outer tubular member having a distal end and an open window disposed at the distal end,
   wherein the open window of the inner tubular member and the open window of the outer tubular member form a cutting tool.

15. The medical device of claim 14 further comprising a spacer between the two separate solenoids.

16. The medical device of claim 14 wherein the two separate solenoids are linearly spaced.

17. The medical device of claim 14 wherein the inner tubular member is configured to be movable relative to the outer tubular member.

18. The medical device of claim 14 further comprising a casing, wherein the two separate solenoids are between the cannulated armature and the casing.

19. The medical device of claim 14 further comprising an armature sleeve, wherein the armature sleeve is between the cannulated armature and the solenoids.

* * * * *